United States Patent [19]

Hoelderich et al.

[11] Patent Number: 4,885,395
[45] Date of Patent: Dec. 5, 1989

[54] PREPARATION OF ALPHA, BETA-UNSATURATED KETONES

[75] Inventors: Wolfgang Hoelderich, Frankenthal; Kurt Schneider, Bad Duerkheim; Leopold Hupfer, Friedelsheim, all of Fed. Rep. of Germany

[73] Assignee: BASF Aktiengesellschaft, Fed. Rep. of Germany

[21] Appl. No.: 100,846

[22] Filed: Sep. 25, 1987

[30] Foreign Application Priority Data

Sep. 25, 1986 [DE] Fed. Rep. of Germany ....... 3632530

[51] Int. Cl.$^4$ ............................................. C07C 45/66
[52] U.S. Cl. .................... 568/314; 568/315; 568/346; 568/347; 568/392; 568/388
[58] Field of Search ............ 568/392, 347, 315, 346, 568/314, 388

[56] References Cited

U.S. PATENT DOCUMENTS

| | | | |
|---|---|---|---|
| 2,312,751 | 3/1943 | Cohen | 568/392 |
| 2,371,577 | 3/1945 | Hale et al. | 568/392 |
| 2,827,490 | 3/1958 | Martin | 568/392 |
| 3,259,658 | 7/1966 | Mercier | 568/392 |
| 3,422,148 | 1/1969 | Wollner et al. | 568/392 |
| 3,890,392 | 6/1975 | Ember | 568/392 |
| 4,512,961 | 4/1985 | Scherzer et al. | 502/79 |

FOREIGN PATENT DOCUMENTS

| | | | |
|---|---|---|---|
| 0046504 | 3/1982 | European Pat. Off. | 502/79 |
| 1383548 | 11/1964 | France | 568/392 |
| 51-125015 | 10/1974 | Japan | 568/392 |
| 0498973 | 1/1939 | United Kingdom | 568/392 |
| 0993389 | 5/1965 | United Kingdom | 568/390 |
| 2008573 | 6/1979 | United Kingdom | 568/314 |
| 2010252 | 6/1979 | United Kingdom | 568/314 |

OTHER PUBLICATIONS

Houben–Weyl, Methoden Der Organischen Chemie, vol. V11/2c, (1977), pp. 2115–2116.
Beilsteins Handuch Der Organischen Chemie, vol. 1, III. 3, (1959), p. 2987, lines 37–40.
Patent Abstract of Japan, 61-5038, vol. 10, No. 144 (C-349), (2201), (1986).

Primary Examiner—James H. Reamer
Attorney, Agent, or Firm—Keil & Weinkauf

[57] ABSTRACT

Alpha,beta-unsaturated ketones of the formula (I)

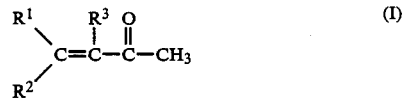

where $R^1$, $R^2$ and $R^3$ are each hydrogen, alkyl, alkenyl of 1 to 12 carbon atoms, cycloalkyl, aryl, aralkyl or alkylaryl, are prepared by converting the corresponding α-hydroxy, alkoxy or carboxy compound in the presence of an acidic catalyst.

Preferred starting materials are 3-methyl-3-hydroxy-butan-2-one, 3-methyl-3-hydroxypentan-2-one and 3-pentamethylene-3-hydroxypropan-2-one, and preferred catalysts are zeolites of the pentasil type.

13 Claims, No Drawings

PREPARATION OF ALPHA, BETA-UNSATURATED KETONES

Bifunctional compounds are useful building blocks for organic syntheses. This class of compounds includes alpha,beta-unsaturated ketones. One of the uses of these ketones is for the synthesis of compounds having physiological activity.

Another field of use for the alpha,beta-unsaturated ketones, in particular methyl isopropenyl ketone, is the chemistry of heat-stable polymers and copolymers. Methyl isopropenyl ketone is used as a monomer for poly(isopropenyl methyl ketone) or as a copolymer with polybutadiene or PVC. Ketones of this type are also used for the preparation of epoxy resins.

It is known that alpha,beta-unsaturated ketones can be prepared by aldol condensation of aliphatic ketones and formaldehyde in the presence of oxalic acid or in the presence of a cation exchanger and H$_2$O under superatmospheric pressure (British Pat. No. 993,389 or French Pat. No. 1,383,548) or by reacting an enol acetate with a ketone in the presence of a Lewis acid, such as BF$_3$ or TiCl$_4$, or by oxidation of branched olefins in 50% strength acetic acid and in the presence of PdCl$_2$ as a catalyst (Belgian Pat. No. 658,801) or by condensation of saturated carbonyl compounds in the presence of BF$_3$.

In addition, there is a multistage process in which alpha,beta-unsaturated ketones are obtained by condensation of ketones in the presence of tosylmethyl isocyanide, followed by alkylation and hydrolysis. Examples of other complicated, expensive preparation processes are the ozonolysis of 2,3-dimethylbutadienes, the anodic oxidation of beta-ketocarboxylates and the photoisomerization of 1,2-diacylcyclobutanes. The gas phase oxidation of olefins over metal oxide/phosphorus oxide catalysts is nonselective and gives a mixture of different compounds, including alpha,beta-unsaturated ketones.

The known processes have various disadvantages: starting compounds which are not readily available are used, toxic and corrosive homogeneous catalysts are employed, or it is necessary to accept an energy-consumptive or multistage reaction procedure, such as ozonolysis or photoisomerization.

It is an object of the present invention to synthesize alpha,beta-unsaturated ketones of the formula (I) by a simple reaction from starting compounds which are more readily available.

We have found that this object is achieved, and that the disadvantages described above are avoided and alpha,beta-unsaturated ketones of the formula (I)

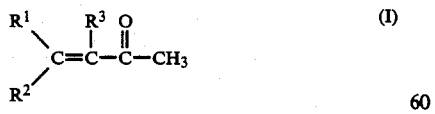

where R$^1$, R$^2$ and R$^3$ are each hydrogen, alkyl and/or alkenyl of 1 to 12 carbon atoms, cycloalkyl, aryl, aralkyl or alkylaryl, which in turn may be substituted, or R$^1$ and R$^3$ or R$^2$ and R$^3$ together with the carbon atoms to which they are bonded may form a cycloalkane or cycloalkene radical, are obtained in a simple manner, if a ketone of the formula (II)

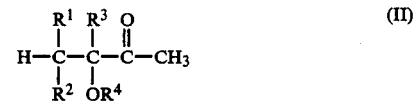

where R$^2$ and R$^3$ have the above meanings and R$^4$ is hydrogen, alkyl or carboxyl, is converted in the presence of an acidic catalyst.

Ketones of the formula (II) which, according to the invention, can be preferably reacted as starting materials are, for example, 3-methyl-3-hydroxybutan-2-one, 3-methyl-3-hydroxypentan-2-one, 3-pentamethylene-3-hydroxypropan-2-one, 3-methyl-3-hydroxyheptan-2-one and 3-phenyl-3-hydroxy-3-methylpropan-2-one. The starting materials can be prepared from tertiary acetyl alcohols, for example by the procedure described in German Pat. No. 1,129,941.

For the purposes of the present invention, catalysts which are generally suitable are zeolites of the pentasil type, such as aluminosilicate zeolites, borosilicate zeolites, iron silicate zeolites and zeolites of the faujasite type.

The zeolites can, for example, be doped with alkali metals, transition metals or rare earth metals.

However, phosphates of the elements B, Al, Zr, Fe or Sr or a mixture of these can also be used as catalysts. For example, hydrothermally prepared phosphates are also suitable as catalysts, e.g. hydrothermally prepared aluminum phosphates, silicon aluminum phosphates or silicon iron aluminum phosphates. Phosphoric acid on carriers can also be used as catalysts.

The zeolites are advantageously used in the acidic form as catalysts for the novel process. Zeolites are crystalline aluminosilicates which have a highly ordered structure with a rigid three-dimensional network of SiO$_4$ and AlO$_4$ tetrahedra which are linked by common oxygen atoms. The ratio of the Si and Al atoms to oxygen is 1:2. The electrovalency of the aluminum-containing tetrahedra is compensated by the inclusion of cations in the crystal, for example an alkali metal or hydrogen ion. Cation exchange is possible. The voids between the tetrahedra are occupied by water molecules prior to dehydration by drying or calcination.

In the zeolites, other elements, such as B, Ga, Fe, Cr, V, As, Sb, Bi or Be or a mixture of these, can also be incorporated in the framework instead of aluminum, or the silicon can be replaced by a tetravalent element, such as Ge, Ti, Zr or Hf.

Zeolites are divided into various groups depending on their structure. For example, the zeolite structure in the mordenite group is formed by chains of tetrahedra and that in the chabasite group is formed by layers of tetrahedra, whereas in the faujasite group the tetrahedra are arranged to form polyhedra, for example in the form of a cubooctahedron, which consists of four-membered rings and six-membered rings. Depending on the way in which the cubooctahedra are linked, giving rise to cavities and pores of different sizes, a distinction is made between zeolites of type A, L, X and Y.

Catalysts which are suitable for the novel process are zeolites of the mordenite group, the fine-pored zeolites of the erionite or chabasite type and zeolites of the faujasite type, e.g. Y, X or L zeolites.

This group of zeolites also includes the ultrastable zeolites of the faujasite type, i.e. dealuminated zeolites.

Processes for the preparation of such zeolites have been described in many publications.

Particularly advantageous zeolites are those of the pentasil type, whose common basic building block is a five-membered ring composed of $SiO_4$ tetrahedra. They are characterized by a high $SiO_2/Al_2O_3$ ratio and by pore sizes which are between those of the zeolites of type A and those of type X or Y.

These zeolites can have different chemical compositions. They are aluminosilicate, borosilicate, iron silicate, beryllium silicate, gallium silicate, chromium silicate, arsenic silicate, antimony silicate and bismuth silicate zeolites and mixtures of these, as well as aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$ and a silicon component, preferably finely divided silica, in aqueous amine solution, in particular in a polyamine, such as 1,6-hexanediamine or 1,3-propanediamine or triethylenetetramine solution, with or, in particular, without the addition of an alkali or alkaline earth, at from 100° to 220° C. under autogenous pressure. These also include the isotactic zeolites according to European Pat. No. 34,727 and European Pat. No. 46,504. The aluminosilicate zeolites obtained have an $SiO_2/Al_2O_3$ ratio of from 10 to 40,000, depending on the amounts of starting materials chosen. Aluminosilicate zeolites of the pentasil type can also be synthesized in an ether medium, such as diethylene glycol dimethyl ether, in an alcoholic medium, such as methanol or butane-1,4-diol, or in water.

The silicon-rich zeolites ($SiO_2/Al_2O_3 \geq 10$) which can be used according to the invention also include the various ZSM types, ferrierite, Nu-1 and Silicalit ®.

Borosilicate zeolites can be synthesized, for example at from 90° to 200° C. under autogenous pressure, by reacting a boron compound, e.g. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These also include the isotactic zeolites according to European Pat. No. 34,727 and European Pat. No. 46,504. Such borosilicate zeolites can also be prepared if the reaction is carried out in solution in an ether, e.g. diethylene glycol dimethyl ether, or in solution in an alcohol, e.g. hexane-1,6-diol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth, at from 100° to 200° C. under autogenous pressure.

The aluminosilicate, borosilicate and iron silicate zeolites prepared in this manner, after being isolated, dried at from 100° to 160° C., preferably 110° C., and calcined at from 450° to 550° C., preferably 500° C., can be molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Advantageous catalysts are also obtained if the aluminosilicate or borosilicate zeolite isolated is molded directly after drying and is subjected to calcination only after the molding procedure. The aluminosilicate and borosilicate zeolites prepared can be employed in pure form, without a binder, as extrudates or pellets, for example ethylcellulose, stearic acid, potato starch, formic acid, oxalic acid, acetic acid, nitric acid, ammonia, amines, silicoesters or graphite, or a mixture of these, being used as extrusion or peptization assistants.

If, because of its method of preparation, the zeolite is present not in the catalytically active, acidic H form but, for example, in the Na form, the latter can be converted completely or partially to the desired H form by ion exchange, for example with ammonium ions, and subsequent calcination, or by treatment with an acid.

If, when the zeolite catalysts are used according to the invention, deactivation occurs as a result of coking, it is advisable to regenerate the zeolites by burning off the coke deposit with air or with an air/$N_2$ mixture at from 400° to 550° C., preferably 500° C. As a result, the zeolites regain their initial activity.

By precoking it is possible to adjust the activity of the catalyst for optimum selectivity with respect to the desired reaction product.

In order to obtain very high selectivity, high conversions and long catalyst lives, it is advantageous to modify the zeolites. In a suitable method of modifying the catalysts, for example, the unmolded or molded zeolites are doped with a metal salt by ion exchange or impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4–8, such as Ti, Zr, V, Nb, Cr, Mo, W, Mn, Re, Fe, Ru, Os, Co, Rh, Sr, Ni, Pd or Pt, transition metals of subgroups 1 and 2, such as Cu, Ag or Zn, and rare earth metals, such as La, Ce, Pr, Nd, Er, Yb or U.

The doping is advantageously carried out as follows: the molded zeolite is initially taken in a riser tube and an aqueous or ammoniacal solution of a halide or nitrate of the metals described above is passed over at from 20° to 100° C. Ion exchange of this type can be carried out using the hydrogen, ammonium or alkali metal form of the zeolite. In another possible method of applying metals to the zeolite, the zeolite material is impregnated with, for example, a halide, a nitrate or an oxide of the metals described above in aqueous, alcoholic or ammoniacal solution. Both ion exchange and impregnation are followed by at least one drying operation and, if desired, by repeated calcination.

In a possible embodiment, for example, $Cu(NO_3)_2 \cdot 3H_2O$ or $Ni(NO_3)_2 \cdot 6H_2O$ or $Ce(NO_3)_3 \cdot 6H_2O$ or $La(NO_3)_2 \cdot 6H_2O$ or $Cs_2CO_3$ is dissolved in water, and this solution is used to impregnate the molded or unmolded zeolite for a certain time, e.g. 30 minutes. Any supernatant solution is freed from water in a rotary evaporator. Thereafter, the impregnated zeolite is dried at about 150° C. and calcined at about 550° C. This impregnation process can be carried out several times in succession in order to obtain the desired metal content.

It is also possible to prepare an aqueous $Ni(CO_3)_2$ solution or ammoniacal $Pd(NO_3)_2$ solution and suspend the pure powdered zeolite therein at from 40 to 100° C. for about 24 hours, while stirring. After the product has been filtered off, dried at about 150° C. and calcined at about 500° C., the zeolite material obtained in this manner can be further processed with or without binder to give extrudates, pellets or fluidizable material.

The zeolite present in the H form or ammonium form or alkali metal form can be subjected to ion exchange as follows: the zeolite, in the form of extrudates or pellets, is initially taken in a column, and, for example, an aqueous $Ni(NO_3)_2$ solution or ammoniacal $Pd(NO_3)_2$ solution is circulated over the said zeolite at slightly elevated temperatures of from 30° to 80° C. for from 15 to 20 hours. The product is then washed thoroughly with water, dried at about 150° C. and calcined at about 550° C. In the case of some metal-doped zeolites, for example Pd-doped, Cu-doped or Ni-doped zeolites, an aftertreatment with hydrogen is advantageous.

In another possible method of modification, the molded or unmolded zeolite material is subjected to a treatment with an acid, such as hydrochloric acid, hydrofluoric acid or phosphoric acid, and/or steam. In an advantageous procedure of this type, for example, the zeolite in powder form is treated with 1N phosphoric acid for 1 hour at 80° C. After the treatment, the product is washed with water, dried at 110° C. for 16 hours and calcined at 500° C. for 20 hours. In another procedure, zeolites, before or after they have been molded with a binder, are treated with a 3-25, in particular 12-20, % strength by weight aqueous hydrochloric acid, for example for from 1 to 3 hours at from 60° to 80° C. The zeolite treated in this manner is then washed with water, dried, and calcined at from 400° to 500° C.

In a particular embodiment of the acid treatment, the zeolite material is treated, before it has been molded, at elevated temperatures with hydrofluoric acid, which is generally used at 0.001-2N, preferably 0.05-0.5 N, hydrofluoric acid, for example by refluxing for, in general, from 0.5 to 5, preferably from 1 to 3, hours. After the zeolite material has been isolated, for example by filtering it off and washing it thoroughly, it is advantageously dried, for example at from 100° to 160° C., and calcined at in general from 450° to 600° C. In another preferred embodiment of the acid treatment, the zeolite material is molded with a binder and then treated at elevated temperatures, advantageously at from 50° to 90° C., preferably from 60° to 80° C., for from 0.5 to 5 hours, preferably with from 12 to 20% strength by weight hydrochloric acid. The zeolite material is then advantageously washed thoroughly, dried at from 100° to 160° C. and calcined at from 450° to 600° C. An HF treatment can also be followed by an HCl treatment.

In another procedure, zeolites can be modified by applying phosphorus compounds, such as trimethoxy phosphate, trimethoxyphosphine or primary, secondary or tertiary sodium phosphate. The treatment with primary sodium phosphate has proven particularly advantageous. In this procedure, the zeolites in the form of extrudates, pellets or fluidizable material are impregnated with aqueous $NaH_2PO_4$ solution, dried at 110° C. and calcined at 500° C.

Other catalysts for the preparation of alpha,beta-unsaturated ketones are phosphates, in particular aluminum phosphates, silicon aluminum phosphates, silicon iron aluminum phosphates, cerium phosphate, zirconium phosphates, boron phosphate, iron phosphate and mixtures of these.

Aluminum phosphate catalysts used for the novel process are, in particular, aluminum phosphates synthesized under hydrothermal conditions. Examples of suitable aluminum phosphates are APO-5, APO-9, APO-11, APO-12, APO-14, APO-21, APO-25, APO-31 and APO-33.

For example, $AlPO_4$-5 (APO-5) is synthesized by mixing orthophosphoric acid with pseudoboehmite (Catapal SB ®) in water to give a homogeneous mixture, adding tetrapropylammonium hydroxide to this mixture and then carrying out the reaction at about 150° C. for from 20 to 60 hours under autogenous pressure in an autoclave. The $AlPO_4$ filtered off is dried at from 100° to 160° C. and calcined at from 450° to 550° C.

$AlPO_4$-9 (APO-9) is likewise synthesized from orthophosphoric acid and pseudoboehmite, in aqueous DABCO (1,4-diazabicyclo[2.2.2]octane) solution at about 200° C. under autogenous pressure in the course of from 200 to 400 hours. If ethylenediamine is used instead of DABCO solution, APO-12 is obtained.

$AlPO_4$-21 (APO-21) is synthesized from orthophosphoric acid and pseudoboehmite in aqueous pyrrolidone solution at from 150° to 200° C. under autogenous pressure in the course of from 50 to 200 hours.

Known silicon aluminum phosphates, such as SAPO-5, SAPO-11, SAPO-31 and SAPO-34, can also be used for the novel process. These compounds are prepared by crystallization from an aqueous mixture at from 100° to 250° C. and under autogenous pressure in the course of from 2 hours to 2 weeks, the reaction mixture comprising a silicon component, an aluminum component and a phosphorus component being reacted in an aqueous solution of an organic amine.

For example, SAPO-5 is obtained by mixing $SiO_2$, suspended in aqueous tetrapropylammonium hydroxide solution, with an aqueous suspension of pseudoboehmite and orthophosphoric acid and then carrying out the reaction at from 150° to 200° C. in the course of from 20 to 200 hours under autogenous pressure in a stirred autoclave. The powder filtered off is dried at from 110° to 160° C. and calcined at from 450° to 550° C.

Other suitable silicon aluminum phosphates are ZYT-5, ZYT-6, ZYT-7, ZYT-9, ZYT-11 and ZYT-12.

Precipitated aluminum phosphates can be used as phosphate catalysts in the process. For example, an aluminum phosphate of this type is prepared by dissolving 92 g of diammonium hydrogen phosphate in 700 ml of water and adding 260 g of $Al(NO_3)_3 \cdot H_2O$ in 700 ml of water dropwise to this solution in the course of 2 hours. The pH is kept at 8 by simultaneously adding 25% strength $NH_3$ solution. The resulting precipitate is stirred for a further 12 hours and then filtered off under suction, washed thoroughly and dried at 60° C. for 16 hours.

Boron phosphates, as catalysts for the novel process, can be prepared, for example, by mixing and kneading concentrated boric acid and phosphoric acid, followed by drying and calcination in an inert gas, air or steam atmosphere at from 250° to 650° C., preferably from 300° to 500° C.

Examples of suitable acidic catalysts are furthermore the acidic oxides of elements of main groups III and IV and subgroups IV to VI of the Periodic Table, in particular oxides such as silica in the form of silica gel, kieselguhr or quartz, as well as titanium dioxide, zirconium dioxide, phosphorus oxides, vanadium pentoxide, niobium oxide, boron trioxide., alumina, chromium oxides, molybdenum oxides, tungsten oxides or mixtures of these oxides.

Catalysts impregnated with phosphoric acid or boric acid can also be used. Phosphoric acid or boric acid is applied to $SiO_2$, $Al_2O_3$ or pumice carriers, for example by impregnation or spraying. A catalyst containing phosphoric acid can be obtained, for example, by impregnating $SiO_2$ with $H_3PO_4$ or $NaH_2PO_4$ or $Na_2HPO_4$ solution and then drying and calcining the product. However, phosphoric acid can also be sprayed together with the silica gel in a spray tower; this is followed by drying and in general calcination. Phosphoric acid can also be sprayed onto the carrier in an impregnating mill.

The catalysts described here can be used alternatively as 2–4 mm extrudates, as pellets having a diameter of 3–5 mm, as chips having particle sizes of 0.1–0.5 mm or as fluidizable catalysts.

In the gas phase, which is preferred, the reaction conditions generally chosen for the novel conversion of the hydroxy-, alkoxy- or carboxyketones are from 100° to 500° C., e.g. from 150° to 450° C., and in particular from 300° to 400° C., and a WHSV of from 0.1 to 20, in particular from 1.0 to 10.0, g of ketone per g of catalyst per hour.

The gas phase reaction can be carried out in a fixed bed or in a fluidized bed.

It is also possible to carry out the reaction in the liquid phase, using the suspension, trickle-bed or liquid phase procedure, at from 50 to 200° C.

The process is carried out batchwise or, preferably, continuously, in general under atmospheric pressure or, depending on the volatility of the starting compound, under reduced or moderately elevated pressure.

Sparingly volatile or solid starting materials can be used in dissolved form, for example in solution in tetrahydrofuran, toluene or petroleum ether. The starting material may furthermore be diluted with solvents of this type or with inert gases such as $N_2$, Ar or steam.

After the reaction, the resulting products are isolated from the reaction mixture by a conventional method, for example by distillation; unconverted starting materials are, if desired, recycled to the reaction.

EXAMPLES 1 to 19

The reaction is carried out in the gas phase under isothermal conditions in a tube reactor (coil, 0.6 cm internal diameter, 90 cm length) for not less than 6 hours. The reaction products are isolated and characterized by conventional methods. Quantitative determination of the reaction products and of the starting materials is carried out by gas chromatography.

The catalysts below are used for the Examples.

Catalyst A

A borosilicate zeolite of the pentasil type is prepared in a hydrothermal synthesis from 640 g of finely divided $SiO_2$, 122 g of $H_3BO_3$ and 8000 g of an aqueous 1,6-hexanediamine solution (50:50 (w/w) mixture) at 170° C. under autogenous pressure in a stirred autoclave. The crystalline reaction product is filtered off and washed thoroughly, after which it is dried at 100° C. for 24 hours and calcined at 500° C. for 24 hours. This borosilicate zeolite is composed of 94.2% by weight of $SiO_2$ and 2.3% by weight of $B_2O_3$. It is molded with a molding assistant to give 2 mm extrudates, which are dried at 110° C. for 16 hours and calcined at 500° C. for 24 hours.

Catalyst B

An aluminosilicate zeolite of the pentasil type is prepared under hydrothermal conditions, under autogenous pressure and at 150° C., from 65 g of finely divided $SiO_2$ and 20.3 g of $Al_2(SO_4)_3 \cdot 18H_2O$ in 1 kg of an aqueous 1,6-hexanediamine solution (50:50 (w/w) mixture) in a stirred autoclave. The crystalline reaction product is filtered off and washed thoroughly, after which it is dried at 110° C. for 24 hours and calcined at 500° C. for 24 hours. The aluminosilicate zeolite contains 96.1% by weight of $SiO_2$ and 4.6% by weight of $Al_2O_3$. The catalyst is converted to 2 mm extrudates, which are dried at 110° C. for 16 hours and calcined at 500° C. for 24 hours.

Catalyst C

An iron silicate zeolite of the pentasil type is synthesized under hydrothermal conditions, under autogenous pressure and at 165° C., from 273 g of waterglass, dissolved in 253 g of an aqueous 1,6-hexanediamine solution (50:50 (w/w) mixture) and 31 g of iron sulfate, dissolved in 21 g of 96% strength sulfuric acid and 425 g of water, in a stirred autoclave in the course of 4 days. The zeolite is filtered off, washed thoroughly, dried at 110° C. for 24 hours and calcined at 500° C. for 24 hours. An iron silicate zeolite having an $SiO_2/Fe_2O_3$ ratio of 17.7 and an $Na_2O$ content of 1.2% by weight is obtained. The zeolite is extruded with finely divided $SiO_2$ in a weight ratio of 80:20 to give 2.5 mm extrudates, which are dried at 110° C. for 16 hours and calcined at 500° C. for 24 hours.

Catalyst D

A commercial Na-Y zeolite is subjected to ion exchange with aqueous $(NH_4)_2SO_4$ solution in a conventional manner until the Na content is less than 0.05% by weight (after drying at 110° C. for 2 hours and calcination at 570° C. for 3 hours).

The powder thus obtained is molded with molding assistants to give extrudates, which are dried at 110° C. and calcined at 500° C. for 16 hours.

Catalyst E

Catalyst E is obtained by impregnating catalyst A with $Ce(NO_3)_3$ solution and then drying the product at 130° C. for 2 hours and calcining it at 540° C. for 2 hours. The Ce content is 1.7% by weight.

Catalyst F

Catalyst F is prepared in the same way as catalyst E, but has a Ce content of 4.1% by weight.

Catalyst G

Catalyst G is prepared in the same way as catalyst E but is impregnated with $Cs_2CO_3$ solution instead of $Ce(NO_3)_3$ solution. The Cs content is 0.7% by weight.

Catalyst H

Catalyst H is obtained by molding the borosilicate zeolite of catalyst A with finely divided $SiO_2$ in a weight ratio of 70:30 to give 2 mm extrudates and drying the latter at 110° C. for 16 hours and calcining them at 500° C. for 16 hours. These extrudates are impregnated with aqueous $NaH_2PO_4$, dried at 110° C. and calcined at 500° C. for 14 hours. The Na content is 5% by weight and the P content 7.5% by weight.

Catalyst I $AlPO_4$-9 (APO-9) is synthesized by dissolving 200 g of 98% strength phosphoric acid, and suspending 136 g of boehmite, in 400 g of water, adding an aqueous solution of 112 g of diazabicyclo[2.2.2]octane (DABCO)

and 320 g of H$_2$O, and reacting this mixture in a stirred autoclave at 200° C. in the course of 336 hours under autogenous pressure. The crystalline material is filtered off, dried at 120° C. and calcined at 500° C. for 16 hours. The AlPO$_4$-9 synthesized in this manner contains 49.0% by weight of P$_2$O$_5$ and 37.1% by weight of Al$_2$O$_3$. This material is molded with an extrusion assistant to give 3 mm extrudates, which are dried repeatedly at 120° C. and calcined at 500° C. for 6 hours.

Catalyst J

SiAlPO$_4$-5 (SAPO-5) is prepared from a mixture of 200 g of 98% strength phosphoric acid, 136 g of boehmite, 60 g of 30% strength silica sol, 287 g of tripropylamine and 587 g of H$_2$O. This mixture is reacted at 150° C. in the course of 168 hours under autogenous pressure. The crystalline product is filtered off, dried at 120° C. and calcined at 500° C. SAPO-5 contains 49.8% by weight of P$_2$O$_5$, 33.0% by weight of Al$_2$O$_3$ and 6.2% by weight of SiO$_2$. SAPO-5 is molded with an extrusion assistant to give 3 mm extrudates, which are dried at 120° C. and calcined at 500° C.

Catalyst K

CePO$_4$ is obtained by precipitation from 52 g of Ce(NO$_3$)$_3$ . 6H$_2$O and 56 g of NaH$_2$PO$_4$ . 2H$_2$O. After filtration, the material is converted to extrudates, dried at 120° C. and calcined at 450° C. Catalyst K contains 47.1% by weight of Ce and 12.7% by weight of P.

Catalyst L

Commercial Zr$_3$(PO$_4$)$_2$ is molded with a molding assistant to give 2 mm extrudates, which are dried at 110° C. and calcined at 500° C. for 16 hours.

Catalyst M

Niobium oxide hydrate is calcined at 300° C. for 2 hours and then molded with finely divided SiO$_2$ in a weight ratio of 70:30 to give 2 mm extrudates, which are dried at 110° C. and calcined at 300° C. for 2 hours.

Catalyst N

Commercial TiO$_2$ is molded with an extrusion assistant to give 2 mm extrudates, which are dried at 110° C. and calcined at 500° C. for 16 hours.

Catalyst O

D 10-10 ®(®=registered trade mark) (Al$_2$O$_3$) is impregnated with H$_3$BO$_3$ dissolved in CH$_3$OH, and is dried at 120° C. and calcined at 500° C. for 15 hours. The boron content is 15% by weight.

The results obtained using catalysts A to O described above, and the reaction conditions, are listed in Table 1 below. The samples were analyzed after a reaction time of 6 hours. Prolonged standing results in the formation of the dimer of isopropenyl methyl ketone. This can be prevented by adding, for example, hydroquinone and by cooling.

TABLE 1

| Example | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Catalyst | A | A | E | F | G | H | B | C | D | I | J | K | L | M | N | O |
| Temperature | 300° C. | 400° C. | 400° C. | 400° C. | 400° C. | 400° C. | 300° C. | 400° C. | 400° C. | 400° C. | 400° C. | 400° C. | 400° C. | 400° C. | 400° C. | 400° C. |
| WHSV | 2 h$^{-1}$ | 2 h$^{-1}$ | 2 h$^{-1}$ | 2 h$^{-1}$ | 2 h$^{-1}$ | 2 h$^{-1}$ | 2 h$^{-1}$ | 3 h$^{-1}$ | 2 h$^{-1}$ | 1 h$^{-1}$ | 2 h$^{-1}$ | 2 h$^{-1}$ | 2 h$^{-1}$ | 2 h$^{-1}$ | 2 h$^{-1}$ | 2 h$^{-1}$ |
| Conversion % | 96.8 | 100 | 100 | 100 | 100 | 99.1 | 100 | 96.4 | 92.5 | 95.3 | 98.3 | 88.3 | 21.5 | 98.7 | 10.3 | 51.2 |
| Selectivity |   |   |   |   |   |   |   |   |   |   |   |   |   |   |   |   |
| I | 88.9 | 87.8 | 96.1 | 92.7 | 89.7 | 94.0 | 95.3 | 79.3 | 94.5 | 92.0 | 53.5 | 87.7 | 99.5 | 57.1 | 84.2 | 45.4 |
| II | 5.7 | 5.3 | 1.2 | 2.0 | 4.4 | 3.0 | 0.1 | 3.6 | — | 1.0 | 15.1 | 1.6 | — | 16.3 | — | — |

The examples (Table 1) show that, among the catalysts for the novel process, zeolites are particularly suitable.

EXAMPLE 17

100 g/h of a mixture of 3-hydroxy-3-methylbutan-2-one and tetrahydrofuran in a weight ratio of 50:50 are completely converted in the course of 10 days in a reactor filled with 100 g of catalyst A and thermostated at 400° C. in a salt bath. Deactivation of the catalyst was still not detected after this time. The results obtained during this time are summarized in Table 2.

TABLE 2

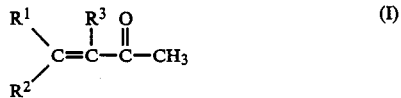

3-Hydroxy-3-methylbutan-2-one $\xrightarrow{-H_2O}$ methylisopropenyl ketone (I)

| Time | 20 h | 52 h | 88 h | 120 h | 152 h | 188 h | 213 h | 240 h |
|---|---|---|---|---|---|---|---|---|
| % by area, I | 89.1 | 90.9 | 92.2 | 93.2 | 93.5 | 94.3 | 94.8 | 94.5 |

EXAMPLE 18

3-Hydroxy-3-methylpentan-2-one is mixed with tetrahydrofuran in a weight ratio of 50:50 and the mixture is completely converted at 400° C. and at WHSV of 1.9 h$^{-1}$ over catalyst A. The liquid mixture discharged contains 75.5% by area of 3-methylpent-3-en-2-one and its isomers.

EXAMPLE 19

3-Pentamethylene-3-hydroxypropan-2-one is mixed with tetrahydrofuran in a weight ratio of 50:50 and completely converted at 400° C. and a WHSV of 4.3 h$^{-1}$ over catalyst B. The liquid mixture discharged contains 67.4% by area of cyclohexenyl methyl ketone and its isomers.

We claim:

1. A process for the preparation of an alpha, beta-unstaturated ketone of the formula I $$\begin{array}{c} R^1 \\ \phantom{R^1}\diagdown \\ \phantom{R^1R^2}C=C-C-CH_3 \\ \phantom{R^1}\diagup \phantom{R^3}\phantom{O} \\ R^2 \end{array} \quad (I)$$

where $R^1$, $R^2$ and $R^3$ are each hydrogen, alkyl, alkenyl of 1 to 12 carbon atoms, cycloalkyl, aryl, aralkyl or alkylaryl, which in turn may be substituted, or $R^1$ and $R^3$ or $R^2$ and $R^3$ together with the carbon atoms to which they are bonded may form a cycloalkane or cycloalkene radical, wherein a hydroxy- alkoxy- or carboxyketone of the formula II

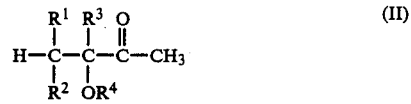

where $R^1$, $R^2$ and $R^3$ have the above meanings and $R^4$ is hydrogen, alkyl or carboxyl, is converted in the gas phase at a temperature of from 100° to 500° C. in the presence of an acidic catalyst selected from the group consisting of a zeolite, a phosphate, a metal oxide and phosphoric acid on a carrier.

2. The process of claim 1, wherein the catalyst used is a zeolite.

3. The process of claim 1, wherein the catalyst used is a zeolite of the pentasil type.

4. The process of claim 1, wherein the catalyst used is an aluminosilicate zeolite of the faujasite type.

5. The process ;of claim 1, wherein a catalyst which is doped with an alkali metal, an alkaline earth metal, a transition metal or a rare earth metal is used.

6. The process of claim 1, wherein the catalyst used is a phosphate.

7. The process of claim 1, wherein the catalyst used is a hydrothermally prepared aluminum phosphate or silicon aluminum phosphate or silicon iron aluminum phosphate or iron aluminum phosphate.

8. The process of claim 1, wherein the catalyst used is an oxide of Al, B, Ti, Zr or Si or a mixture of these.

9. The process of claim 1, wherein the catalyst used is phosphoric acid or pumice or silica or alumina, or boric acid on pumice or silica or alumina.

10. The process of claim 1, wherein the ketone (II) is selected from the group consisting of 3-methyl-3-hydroxybutan-2-one, 3-methyl-3-hydroxypentan-2-one, 3-pentamethylene-3-hydroxypropan-2-one, 3-methyl-3-hydroxyheptan-2-one and 3-phenyl-3-hydroxy-3-methyl-propan-2-one.

11. The process of claim 10, wherein the catalyst is a zeolite of the pentasil type.

12. The process of claim 1, wherein $R^4$ of the ketone (II) is hydrogen.

13. The process of claim 12, wherein the acidic catalyst is a borosilicate zeolite of the pentasil type.

* * * * *